United States Patent [19]
Makino et al.

[11] Patent Number: 5,932,593
[45] Date of Patent: Aug. 3, 1999

[54] PIPERIDINE DERIVATIVES AND ANTI-PLATELET AGENTS CONTAINING THE SAME

[75] Inventors: Shingo Makino; Harumi Arisaka; Hiroshi Yamamoto; Masataka Shoji; Ryota Yoshimoto, all of Kawasaki, Japan

[73] Assignee: Ajinomoto Co., Ltd., Tokyo, Japan

[21] Appl. No.: 08/917,180

[22] Filed: Aug. 25, 1997

Related U.S. Application Data

[63] Continuation of application No. 08/425,645, Apr. 20, 1995, abandoned.

[30] Foreign Application Priority Data

Apr. 20, 1994 [JP] Japan ..................... 6-081499

[51] Int. Cl.⁶ ............ A61K 31/445; C07D 401/12
[52] U.S. Cl. ............ 514/316; 514/183; 514/185; 514/188; 544/1; 544/106; 544/361; 544/364; 546/191
[58] Field of Search .................. 514/183, 185, 514/188, 316; 544/1, 106, 361, 364; 546/191

[56] References Cited

U.S. PATENT DOCUMENTS

| 5,229,400 | 7/1993 | Hirasawa et al. .......... 514/325 |
| 5,250,681 | 10/1993 | Shoji et al. . |
| 5,393,890 | 2/1995 | Syoji et al. . |

FOREIGN PATENT DOCUMENTS

| 0 307 303 | 3/1989 | European Pat. Off. . |
| 0 371 805 | 6/1990 | European Pat. Off. . |
| 0 406 739 | 1/1991 | European Pat. Off. . |
| 0 479 601 | 4/1992 | European Pat. Off. . |
| 1 322 527 | 2/1963 | France . |

OTHER PUBLICATIONS

Richardson, B.P. et al, Nature, Jul. 1985, 316, pp. 126–131.
Kuruvilla, A. et al, Ind. J. Physiol. Pharmacol. 1973, 17(2), pp. 111–116. (Abstract).
Williams, F.M. et al J. Cardiovasc. Pharmacol. (May–Jun. 1985), 7(3), pp. 550–555. (Abstract).
Morganroth, J. et al Am. J. Card. (Feb. 15, 1988), 61(6), pp. 470–471. (Abstract).
Scholtysik, G. et al J. Pharm. Exp. Ther. (Jun. 1988), 245(3), pp. 773–778. (Abstract).
Gleerup, G. et al Eur. J. Clin. Pharm. 1993, 44(2), pp. 121–125. (Abstract).
Vanhoutte, P.M. et al Neth. J. Med. (Feb. 1991), 38(1–2), pp. 35–42. (Abstract.
Goodman, A. et al., The Pharmacological Basis of Therapeutics, 8th ed., Pergamon Press, 1990, pp. 592–593.
Weissman, A., in Serotonin and Behavior, edited by Barchas, J. et al, 1973, Academic Press, pp. 235–248.
Glennon, R.A., J. Med. Chem. 1987, 30(1), pp. 1–12.

*Primary Examiner*—Ceila Chang
*Assistant Examiner*—Rita Desai
*Attorney, Agent, or Firm*—Oblon, Spivak, McClelland, Maier & Neustadt, P.C.

[57] ABSTRACT

The present invention also relates to a method of using these novel materials, and other materials, to treat or prevent a disease caused by serotonin or a method of treating or preventing platelet aggregation. The compounds used are piperidine derivatives having the formula (I):

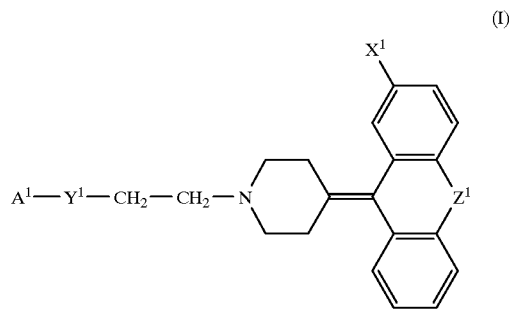

wherein the various substituents are defined below.

10 Claims, No Drawings

PIPERIDINE DERIVATIVES AND ANTI-PLATELET AGENTS CONTAINING THE SAME

This application is a continuation of application Ser. No. 08/425,645, filed on Apr. 20, 1995, now abandoned.

BACKGROUND OF THE INVENTION

1. Field of the Invention

The present invention relates to a novel serotonin antagonist and an anti-platelet agent, more particularly, a serotonin antagonist and an anti-platelet agent which potently and specifically inhibit the serotonin 2 receptor with low adverse side effect.

2. Discussion of the Background

It is believed that the thrombus greatly participates in ischemic disorders such as cardiac infarction and cerebral infarction and, in particular, the platelet plays an important role in the formation of the arterial thrombus. Known anti-platelet agents include arachidonic acid metabolism-inhibiting agents, platelet cyclic nucleoside-related agents, thromboxane receptor antagonists. Aspirin and ticlopidine have also been clinically used. However, the effect of these agents is not sufficient and thus development of more effective agents has been in demand.

It is known that serotonin (5HT), which is stored in α granules of the platelet, is released by activation of the platelet caused by various stimulations, and the released serotonin increases the calcium ion level in the cell via the serotonin 2 ($5HT_2$) receptor on the platelet membrane, resulting in aggregation of the platelet. It is believed that the $5HT_2$ receptor existing in the vascular smooth muscle participates in the blood vessel contraction. Accordingly, the $5HT_2$ receptor antagonist is expected to have vasoconstriction inhibiting activity in addition to the platelet aggregation inhibiting activity and, therefore, may also have potent anti-thrombus function.

SUMMARY OF THE INVENTION

Accordingly, one object of this invention is to provide a novel serotonin antagonist and an anti-platelet agent which potently and specifically inhibit the serotonin 2 receptor with low adverse side effect.

This and objects which will become apparent hereinafter have been achieved with the following novel serotonin agents.

DESCRIPTION OF THE PREFERRED EMBODIMENTS

The present invention relates to a serotonin antagonist or an anti-platelet agent which comprises as an active ingredient a piperidine derivative represented by the following general formula (I):

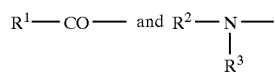

wherein $A^1$ represents an unsubstituted or substituted pyridyl, piperidyl, piperidino, morpholinyl, morpholino, thiomorpholinyl, thiomorpholino or piperazinyl group, a substituted alkyl group having from 1 to 8 carbon atoms, a substituted cycloalkyl group having from 4 to 8 carbon atoms, or an unsubstituted or substituted alkoxyl group having 1 to 8 carbon atoms, $X^1$ represents a hydrogen atom or a halogen atom selected from the group consisting of bromine, chlorine, flourine and iodine, $Y^1$ represents one of the following organic groups:

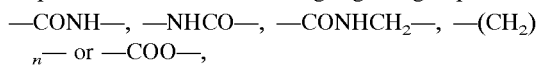

wherein n is an integer of from 0 to 4, and $Z^1$ represents one of the following organic groups:

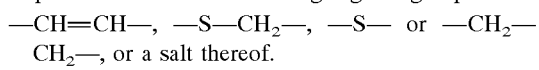

or a salt thereof.

Preferred substituents for $A^1$ in the above general formula (I) include:

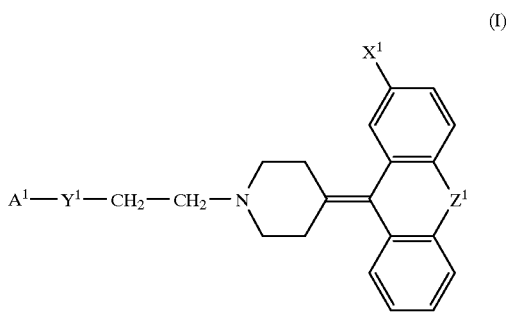

wherein $R^1$ is a hydrogen atom, an alkyl or alkoxyl group having from 1 to 6 carbon atoms, an amino group which may be substituted by an alkyl group having from 1 to 6 carbon atoms, or an acylaminoalkyl group having from 1 to 6 carbon atoms, and $R^2$ and $R^3$, which may be the same or different, each represents a hydrogen atom, an alkyl, acyl or alkoxycarbonyl group having from 1 to 6 carbon atoms, or an aminocarbonyl group which may be substituted by an alkyl group having from 1 to 6 carbon atoms.

Illustrative examples of such preferred substituents of $A^1$ include formyl, acetyl, propionyl, butyryl, isobutyryl, valeryl, isovaleryl, pivaloyl, carbamoyl, N-methylcarbamoyl, N-ethylcarbamoyl, N-propylcarbamoyl, N,N-dimethylcarbamoyl, N,N-diethylcarbamoyl, N-formylglycyl, N-acetylglycyl, N-formyl-o-alanyl, N-acetyl-N-alanyl, N-methyl-N-formyl, N-mothyl-N-acetyl, N-methyl-N-propionyl, N-ethyl-N-formyl and N-ethyl-N-acetyl.

Preferred examples of $Y^1$ in the general formula (I) include a group —CONH—.

Preferred examples of $Z^1$ include —CH=CH—.

Among the compounds represented by the general formula (I), the compounds represented by the following general formula (II) are novel compounds.

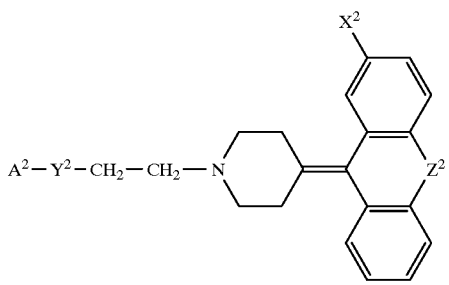

(II)

wherein
  $A^2$ represents an unsubstituted or substituted piperidyl, piperidino, morpholinyl, morpholino, thiomorpholinyl, thiomorpholino or piperazinyl group, a substituted alkyl group having from 1 to 8 carbon atoms, a substituted cycloalkyl group having from 4 to 8 carbon atoms, or an unsubstituted or substituted alkoxyl group having 1 to 8 carbon atoms.

When $A^2$ has a substituent, the substituent is one of the following groups.

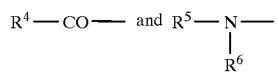

wherein
  $R^4$ represents an alkyl or alkoxyl group having from 1 to 6 carbon atoms, an amino group which may be substituted by an alkyl group, or an acylaminoalkyl group, and
  $R^5$ and $R^6$, which may be the same or different, each represents a hydrogen atom, an alkyl, acyl or alkoxycarbonyl group having from 1 to 6 carbon atoms, or an aminocarbonyl group which may be substituted by an alkyl group, and
  $X^2$, $Y^2$, and $Z^2$, respectively, have the same meanings as $X^1$, $Y^1$, and $Z^1$.

Preferred substituents for $A^2$ include acetyl, propionyl, butyryl, isobutyryl, valeryl, isovaleryl, pivaloyl, carbamoyl, N-methylcarbamoyl, N-ethylcarbamoyl, N-propylcarbamoyl, N,N-dimethylcarbamoyl, N,N-diethylcarbamoyl, N-formylglycyl, N-acetylglycyl, N-formyl-β-alanyl, N-acetyl-β-alanyl, N-methyl-N-formyl, N-methyl-N-acetyl, N-methyl-N-propionyl, N-ethyl-N-formyl, N-ethyl-N-acetyl, and the like.

Preferably, $Y^2$ is a group —CONH—.
Preferably, $Z^2$ is a group —CH=CH—.

The piperidine derivative represented by the above general formula (I) may be prepared by the conventional method, for example, by the method described in an unexamined published Japanese patent application 3-47168, incorporated herein by reference.

For example, 4-(5H-dibenzo[a,d]cyclohepten-5-ylidene-1-(2-t-butoxycarbonylamino)ethyl)piperidine (compound (3)) included in the general formula (I) can be easily obtained by subjecting N-t-butoxycarbonyl-2-bromoethylamine (compound (1)) and 4-(5H-dibenzo[a,d]cyclohepten-5-ylidene)piperidine (compound (2)) to the condensation reaction in the presence of a base such as triethylamine, as shown in the Reaction Scheme I.

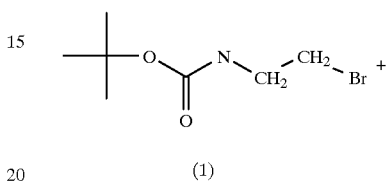

(1)

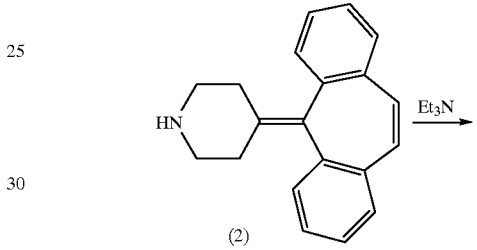

(2)

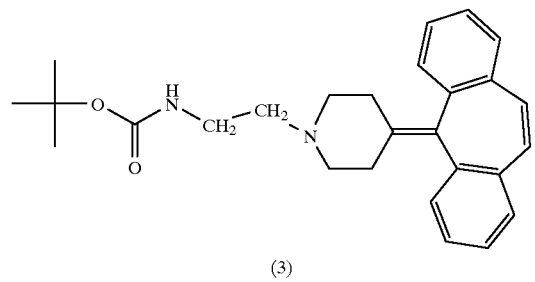

(3)

Similarly, 1-formyl-N-(2-(4-(5H-dibenzo[a,d]cyclohepten-5-ylidene)-1-piperidinyl))ethylisonipecotamide (compound (6)) included in the general formula (I) can be easily obtained by subjecting the compound 4, which is obtained by removing a t-butoxycarbonyl group from the compound 3 using 4 M hydrochloric acid/dioxane, etc., and 1-formylisonipecotic acid (compound (5)) to the condensation reaction using a condensation agent such as 1-(3-dimethylaminopropyl)-3-ethlcarbodiimide, as shown in the Reaction Scheme II.

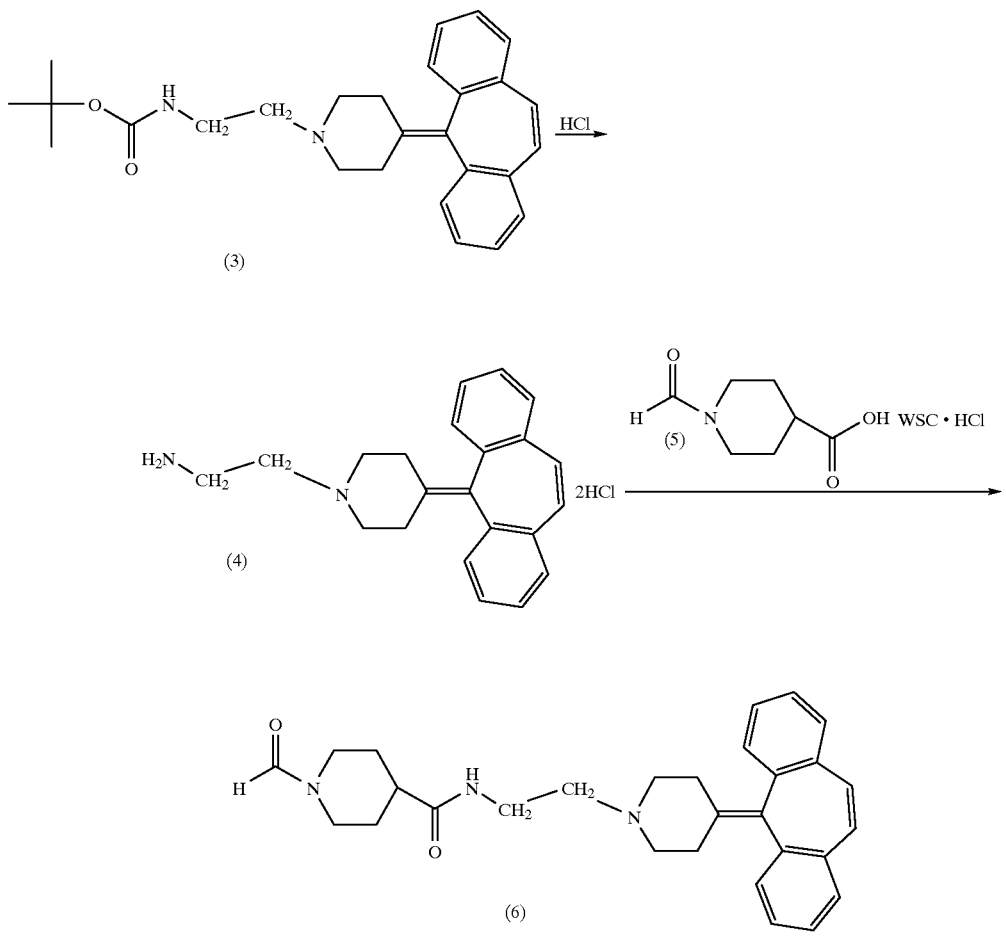

The reaction product obtained by these production methods is isolated and purified as a free compound or a salt thereof. Isolation and purification may be carried out by extraction, concentration, evaporation, crystallization, and various types of chromatography.

Examples of the salt of the piperidine derivative include acid addition salts with inorganic acid such as hydrochloric acid, hydrobromic acid, sulfuric acid, nitric acid, and phosphoric acid and with organic acids such as formic acid, acetic acid, lactic acid, salicylic acid, mandelic acid, citric acid, oxalic acid, maleic acid, fumaric acid, tartaric acid, tannic acid, malic acid, p-toluenesulfonic acid, methanesulfonic acid, and benzenesulfonic acid.

The piperidine derivative represented by the general formula (I) exhibits a serotonin antagonizing activity and is useful as an agent for the treatment of ischemic disorders, thrombosis, obstruction, mental diseases (depression, anxiety), diabetic complication, arteriosclerosis, hypertension, arrhythmia, migraine, microcirculation failure, and the like. In particular, as an anti-platelet agent, the piperidine derivative represented by the general formula (I) is useful as an agent for the treatment of various ischemic disorders, thrombosis, obstruction, angiitis, diabetic complication, arteriosclerosis, nephropathy, and ulcer, pain, rhigosis, etc. due to chronic arterial obstruction, and also can be used as a treating agent for improving various ischemia accompanying circulation failure, for preventing restenosis after surgical treatment of ischemic heart diseases, and for improving blood circulation.

When the piperidine derivative of the general formula (I) is used as a serotonin antagonist or an anti-platelet agent, the administration route may be either oral or parenteral. Though the clinical dose may differ depending on the age, body weight, and condition of the patient and on the administration method, but the dose per an adult per day is generally from 0.01 mg to 500 preferably from 0.1 mg to 50 mg in the case of oral administration and 1 $\mu$g to 100 mg preferably from 0.01 mg to 10 mg in the case of parenteral administration.

As the dosage form, usual dosage forms such as tablets, powders, sugar-coated preparations, capsules and solutions may be employed and such dosage forms can be prepared by the conventional method making use of usual pharmaceutical adjuvants.

This application is based on Japanese Patent Application No. 081499/1994, the text of which is incorporated herein by reference.

EXAMPLES

Having generally described this invention, a further understanding can be obtained by reference to certain specific examples which are provided herein for purposes of illustration only and are not intended to be limiting unless otherwise specified.

Preparation Procedure A

Synthesis of 1-methoxycarbonyl-N-(2-(4-(5H-dibenzo [a,d]cyclohepten-5-ylidene)-1-piperidinyl)) ethylisonipecotamide hydrochloride

Step 1

Synthesis of 2-t-Butoxycarbonylaminoethylbromide

2-Aminoethylbromide hydrobromide (35.77 g, 174.6 mmol) and di-t-butyl dicarbonate (22.80 g, 104.5 mmol) were added to a mixed solvent of 300 ml of diethyl ether and 300 ml of water. Then, sodium hydrogencarbonate (44.00 g, 523.7 mmol) was gradually added and the mixture was stirred at room temperature overnight. The diethyl ether layer was washed with 80 ml of 1 N hydrochloric acid and then with 80 ml of a saturated aqueous sodium chloride solution, and dried over magnesium sulfate powder. The solvent was evaporated to obtain the titled compound.
Amount obtained: 21.57 g (96.25 mmol); Yield: 92%

Step 2

Synthesis of 4-(5H-dibenzo[a,d]cyclohepten-5-ylidene)-1-(2-t-butoxycarbonylamino)ethyl) piperidine 2-t-Butoxycarbonylaminoethylbromide (4.5 g, 20.1 mmol), 4(5H-dibenzo[a,d]cyclohepten-5-ylidene)piperidine (2.7 g, 10.0 mmol), and triethylamine (4.2 ml, 30 mmol) were added to acetonitrile (300 ml), and the mixture was stirred on an oil bath at 50° C. for 16 hours. The temperature was lowered to room temperature, the solvent was evaporated, and the residue was dissolved in 300 ml of ethyl acetate. After removing insoluble matters by filtration, the filtrate was washed with 100 ml of 1 N hydrochloric acid, 100 ml of a 1 N aqueous sodium hydroxide solution, and 100 ml of a saturated sodium chloride aqueous solution, and dried over magnesium sulfate powder. The solvent was evaporated and the residue was purified by silica gel column chromatography to obtain the titled compound.
Amount obtained: 3.6 g (8.6 mmol); Yield: 86%

Step 3

Synthesis of 1-(2-aminoethyl)-4-(5H-dibenzo [a,d] cyclohepten-5-ylidene)piperidine dihydrochloride 4-(5H-Dibenzo[a,d]cyclohepten-5-ylidene)-1-(2-t-butoxycarbonylamino) ethyl)piperidine (8.47 g, 20.4 mmol) was dissolved in 100 ml of dichloromethane, and 100 ml of a 4 N hydrochloric acid-dioxane solution was added thereto, followed by stirring at room temperature for 1 hour. The solvent was evaporated to obtain the titled compound (8.56 g).

Step 4

Synthesis of 1-t-butoxycarbonyl-N-(2-(4-(5H-dibenzo[a,d]cyclohepten-5-ylidene)-1-piperidinyl)) ethylisonipecotamide 1-(2-Aminoethyl)-4-(5H-dibenzo[a,d]cyclohepten-5-ylidene) piperidine dihydrochloride (2.3 g, 6.0 mmol), 1-t-butoxycarbonylisonipecotic acid (1.6 g, 7.2 mmol), triethylamine (3.0 ml, 21.6 mmol) and 1-ethyl-3-(3-dimethlaminopropyl) carbodiimide hydrochloride (1.4 g, 7.2 mmol) were mixed, and the mixture was stirred at room temperature overnight. After evaporating the solvent, the residue was dissolved in 100 ml of dichloromethane, washed with 100 ml of 1 N hydrochloric acid, 100 ml of a 1 N aqueous, sodium hydroxide solution, and 50 ml of a saturated aqueous sodium chloride solution. The solvent was evaporated and the residue was purified by silica gel chromatography to obtain the titled compound.

Amount obtained: 2.0 g (3.8 mmol); Yield: 63i

Step 5

Synthesis of N-(2-(4-(SH-dibenzo[a,d]cyclohepten-5-ylidene) 1-piperidinyl))ethylisonipecotamide dihydrochloride 10 ml of 4 N hydrochloric acid-dioxane solution was added to 1-t-butoxycarbonyl-N- (2-(4-(5H-dibenzo[a,d] cyclohepten-5-ylidene)-1-piperidinyl)) ethylisonipecotamide (0.10 g, 0.185 mmol), and the mixture was stirred at room temperature for 1 hour. The solvent was evaporated to obtain the titled compound.

Amount obtained: 0.093 g (0.186 mmol); Yield: 100%

Step 6

Synthesis of 1-methoxycarbonyl-N-(2-(4-(5H-dibenzo [a,d]cyclohepten-5-ylidene-1-piperidinyl)) ethylisonipecotamide hydrochloride N-(2-(4-(5H-Dibenzo[a,d]cyclohepten-5-ylidene)-1-piperidinyl)) ethylisonipecotamide dihydrochloride (0.59 g, 1.18 mmol) and triethylamine (0.8 ml, 5.70 mmol) were dissolved in 50 ml of dichloromethane, and methyl chloroformate (0.1 ml, 1.40 mmol) was added. The mixture was stirred for 1 hour and 100 ml of dichloromethane was added. The mixture was washed with 70 ml of water, 70 ml of a 1 N aqueous sodium hydroxide solution, and 70 ml of a saturated aqueous sodium chloride solution, and purified by silica gel chromatography. The product obtained was converted into the hydrochloride form to give the titled compound. Amount obtained: 0.39 g (0.75 mmol); Yield: 63%

The compounds shown in Table 1 were produced by the similar manner as described in Preparation procedure A.

| | A | Y | X | Z | pKi | pIC$_{50}$ |
|---|---|---|---|---|---|---|
| 1 | CH$_3$OCO—N(4-Me-piperidine) | —CONH— | H | —CH=CH— | 8.2 | 7.5 |
| 2 | H—N(4-Me-piperidine) | | | | 8.6 | 7.3 |
| 3 | HCO—N(4-Me-piperidine) | | | | 8.4 | 7.2 |
| 4 | CH$_3$CO—N(4-Me-piperidine) | | | | 8.5 | 7.2 |
| 5 | (CH$_3$)$_3$COCO—N(4-Me-piperidine) | | | | 8.0 | 6.5 |
| 6 | H$_2$NCO—N(4-Me-piperidine) | | | | — | 6.9 |
| 7 | (CH$_3$)$_2$NCO—N(4-Me-piperidine) | | | | 8.5 | 6.7 |
| 8 | CH$_3$CONHCH$_2$CO—N(4-Me-piperidine) | | | | 7.9 | 6.6 |
| 9 | H—N(2-Me-piperidine) | | | | 7.8 | 7.1 |
| 10 | CH$_3$CO—N(2-Me-piperidine) | | | | 8.8 | — |
| 11 | HCO—N(4-Me-piperazine) | | | | 8.8 | 7.0 |

-continued

[Structure: A—Y—CH₂—CH₂—N(piperidine)=C(xanthene with X and Z substituents)]

| | A | Y | X | Z | pKi | pIC$_{50}$ |
|---|---|---|---|---|---|---|
| 12 | H₂N-cyclohexyl- | | | | 8.6 | 6.6 |
| 13 | CH₃CONH-cyclohexyl- | | | | 9.3 | — |
| 14 | (CH₃)₃COCONH-cyclohexyl- | —CONH— | H | —CH=CH— | — | — |
| 15 | 4-pyridyl-CH₂- | | | | — | — |
| 16 | CH₃CH₂O— | | | | — | 7.6 |
| 17 | (CH₃)₃CO— | | | | — | 7.0 |
| 18 | 1-methyl-1-(NH₂)-cyclohexyl | | | | 8.9 | 7.3 |
| 19 | 1-methyl-1-(NHCOCH₃)-cyclohexyl | | | | 8.3 | 6.4 |
| 20 | 1-methyl-1-(NHCOOC(CH₃)₃)-cyclohexyl | | | | 8.0 | 6.3 |
| 21 | 1-methyl-1-(NHCHO)-cyclohexyl | | | | 7.8 | 6.5 |
| 22 | 1-methyl-1-(NHCON(CH₃)₂)-cyclohexyl | | | | 8.2 | 5.8 |
| 23 | H₂N(CH₂)₃— | | | | — | 7.6 |
| 24 | HCONH(CH2)₃— | | | | 9.8 | 7.2 |
| 25 | CH₃CONH(CH₂)₃— | | | | 9.2 | 6.6 |
| 26 | (CH₃)₃COCONH(CH₂)₃— | | | | — | 7.2 |
| 27 | (CH₃)₂NCONH(CH₂)₃— | —CONH— | H | —CH=CH— | 9.2 | 6.9 |
| 28 | CH₂NH(CH₂)₃— | | | | — | 6.6 |
| 29 | (CH₃)₃COCON(CH₂)₃—CH₃ | | | | — | 7.1 |

-continued

[Structure: A—Y—CH₂—CH₂—N(piperidinyl)=dibenzo[a,d]cycloheptene with X and Z substituents]

| # | A | Y | X | Z | pKi | pIC$_{50}$ |
|---|---|---|---|---|---|---|
| 30 | HCO—N(piperidinyl)— | —CONHCH$_2$— | | | 8.3 | 6.4 |
| 31 | $(CH_3)_3CO$— | | | | 8.8 | — |
| 32 | $H_2N$— | —CH$_2$— | | | — | — |
| 33 | HCO—N(piperidinyl)— | —COO— | | | 8.3 | 7.4 |
| 34 | $H_2N$— | — | | —CH$_2$—CH$_2$— | — | — |
| 35 | $(CH_3)_3CO$— | —CONH— | | | 8.3 | — |
| 36 | HCO—N(piperidinyl)— | | | | 8.9 | 5.8 |
| 37 | $H_2N$— | — | | —S— | 8.4 | 5.0 |
| 38 | $(CH_3)_3CO$— | —CONH— | | | 9.1 | 7.3 |
| 39 | HCO—N(piperidinyl)— | | | | 9.2 | 7.1 |
| 40 | HCO—N(piperidinyl)— | | F | —S—CH$_2$— | 7.1 | 5.6 |

Preparation Procedure B

Synthesis of 1-(4-(4-(5H-dibenzo[a,d]cyclohepten-5-ylidene)-1-piperidinyl) butyl)morpholine Step 1

Synthesis of 1-(4-oxo-4-morpholinobutyryl)-4-(5H-dibenzo [a,d]cyclohepten-5-ylidene)piperidine In 50 ml of dichloromethane, 4-(5H-dibenzo [a,d] cyclohepten-5-ylidene)piperidine (0.27 g, 1.0 mmol), succinic anhydride (0.12 g, 1.2 mmol), and triethylamine (0.17 ml, 1.2 mmol) were stirred at room temperature overnight. Morpholine (0.14 ml, 1.6 mmol) and 1-ethyl-3-(3-dimethylaminopropyl)carbodiimide hydrochloride (0.27 g, 1.4 mmol) were added and the mixture was further stirred at room temperature for 8 hours. The reaction mixture was washed with 30 ml of 1 N hydrochloric acid, 30 ml of a 1 N aqueous sodium hydroxide solution, and 30 ml of a saturated aqueous sodium chloride solution, dried over magnesium sulfate powder, and purified by silica gel chromatography to obtain the titled compound. Amount obtained: 0.44 g (1.0 mol); Yield: 100%

Step 2

Synthesis of 1-(4-(4-(5H-dibenzo[a,d]cyclohepten-5-ylidene) 1-piperidinyl)butyl)morpholine dihydrochloride In tetrahydrofuran (60 ml), 1-(4-oxo-4-morpholinobutyryl)-4-(5H-dibenzo[a,d]cyclohepten-5-ylidene)piperidine (0.44 g, of 1.00 mmol) was reacted with lithium aluminum hydride (0.38 g, 10.0 mol) at 0° C., and further treated in accordance with the conventional method to obtain the titled compound.

Amount obtained: 0.32 g (0.66 mmol); Yield: 66%

The compounds shown in Table 2 were produced by the similar manner as described in Preparation procedure B.

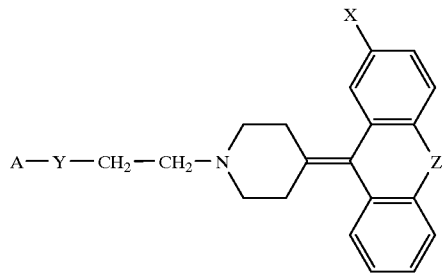

| | A | Y | X | Z | pKi | pIC$_{50}$ |
|---|---|---|---|---|---|---|
| 41 | morpholine (O) | —(CH$_2$)$_2$— | H | —CH=CH— | 8.2 | 6.9 |
| 42 | thiomorpholine (S) | | | | 8.7 | 6.6 |
| 43 | piperidine | —(CH$_2$)$_3$— | | | 7.3 | — |
| 44 | piperidine | —(CH$_2$)$_2$— | | —CH$_2$—CH$_2$— | 7.9 | — |
| 45 | piperidine | | | —S— | 8.1 | — |

Test Example 1

The binding affinity to the serotonin 2 receptor was evaluated using a bovine cerebral cortex membrane sample. To 200 μl of a bovine membrane sample adjusted to 50 mg (wet weight) membrane/ml were added 200 μl of 3 nM [$^3$H]-ketanserin and 200 μl of a test compound solution prepared by dissolving a test compound in 1.7% ethanol, followed by mixing. The mixture was incubated at 25° C. for 30 minutes and filtered with a glass filter. The radioactivity trapped on the filter was measured with a liquid scintillation counter. The non-specific binding was defined by 10$^{-6}$ M LY53857. The concentration of the test compound which inhibits 50% of the specific binding of [$^3$H]-ketanserin (i.e., IC$_{50}$ value) was obtained, and the Ki value was calculated in accordance with the following equation. The results are shown as the negative logarithm of the Ki value (i.e., pKi value).

$$K_i = \frac{IC_{50}}{1 + \frac{[L]}{K_d}}$$

In the equation, Ki indicates the dissociation constant and [L] indicates the concentration of [$^3$H]-ketanserin.

From the results in Tables 1 and 2, it is apparent that the piperidine derivative of the present invention exhibits strong binding affinity to the serotonin 2 receptor.

Test Example 2

The anti-platelet effect due to the serotonin antagonistic activity was measured in vitro using the platelet of SD rats (body weight: about 300 to 400 g, male). Platelet rich plasma (PRP) and platelet poor plasma (PPP) were prepared from blood with 0.38t sodium citrate which was obtained from aorta abdominalis of a rat under diethyl ether anesthesia. The platelet concentration of PRP was adjusted to 5×10$^8$ platelets/ml by adding PPP. Then, the test compound dissolved in 0.4t aqueous ethanol was added, and the mixture was incubated at 37° C. for 3 minutes. The platelet aggregation induced by addition of 0.5 μM or 0.8 μM adenosine diphosphate (ADP) +serotonin was measured as an increase in optical transmittance of PRP. The concentration of the test compound which inhibits 50% of the increase in platelet aggregation which is obtained with serotonin without a test compound was measured, and its negative logarithm (pIC$_{50}$) was calculated. The results are shown in the Table 1 and 2. From these results, it is apparent that the piperidine compound of the present invention potently inhibits the platelet aggregation by serotonin.

Test Example 3

The anti-platelet effect due to the serotonin antagonistic activity was measured in vivo using SD rats (body weight: about 210 to 330 g, male). The test compound was dissolved or suspended in arabic gum and orally administered to the rat in a dose shown in Table 3. Two hours after the administration of the test compound, the rat was anesthetized with diethyl ether and platelet rich plasma (PRP) and platelet poor plasma (PPP) were prepared from blood with 0.38% sodium citrate which was obtained from aorta abdominalis of the rat. The platelet concentration of PRP was adjusted to $5 \times 10^8$ platelets/ml by adding PPP. Then, the PRP was incubated at 37° C. for 3 minutes, and platelet aggregation induced by addition of 0.7 $\mu$M adenosine diphosphate (ADP)+serotonin was measured as an increase in optical transmittance of PRP. The aggregation occurred by addition of ADP alone and the maximum aggregation ratio by the simultaneous addition of ADP and serotonin were measured with respect to each group, and increase in aggregation caused by serotonin was calculated. The increase in aggregation caused by serotonin in the arabic gum administered group was taken as 100%, and the effect of the test compound was judged using as an index the increase in aggregation caused by the serotonin in the test compound-administered group (n=3). The results are shown in the Table 3.

| Test Compound | Amount of administration (mg/kg) | Increase in aggregation by serotonin (%) |
|---|---|---|
| arabic gum | — | 100 |
| compound of No. 3 | 0.1 | 75.7 |
|  | 0.3 | 57.3 |
|  | 1 | 24.3 |
|  | 3 | 27 |
|  | 10 | −2.7 |
| compound of No. 9 | 0.3 | 57.3 |
| compound of No. 17 | 0.3 | 50.7 |
| compound of No. 18 | 0.3 | 94.9 |
| compound of No. 38 | 0.3 | 82.4 |
| compound of No. 39 | 0.3 | 54.5 |
| compound of No. 41 | 0.3 | 91.5 |

From the results in the Table 3, it is apparent that the piperidine compound of the present invention potently inhibits the platelet aggregation by serotonin even in the case of oral administration.

Test Example 4

The serotonin antagonistic activity in the central nerve system was evaluated by measuring the inhibiting effect on head twitch of mouse induced by 5-hydroxytryptophan (5HTP) A test compound in an amount of 1, 3, 10, or 30 mg was respectively dissolved in 100 ml of water and, 90 minutes before 5HTP administration, the solution (10 ml/kg body weight) was orally administered to a ICR mouse (body weight: 27 to 32 g, male) fasted from the previous day. As a control, 5% arabic gum was used. Carbidopa (6 mg/kg) was subcutaneously administered and, after 15 minutes, 5HTP (180 mg/kg) was intraperitoneally administered. From the 15 minutes after 5HTP administration, the number of head twitches occurred within 2 minutes were counted. The concentration of the test compound which inhibits 50% of the number of head twitches in the 5% arabic gum administered group was obtained. The results are shown in the Table 4.

TABLE 4

| Test compound | $ID_{50}$ (mg/kg) |
|---|---|
| compound of No. 3 | 0.39 |
| cycloheptadine | 0.12 |

From the results in the Table 4, it is apparent that the piperidine compound of the present invention has low effect on the central nerve system and is a highly safe compound.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A pharmaceutical composition effective in treating conditions mediated by serotonin release, comprising a5HT$_2$ receptor antagonistic effective amount of a compound, or a pharmaceutically acceptable salt thereof, and a pharmaceutically acceptable carrier, wherein said compound has the following formula:.

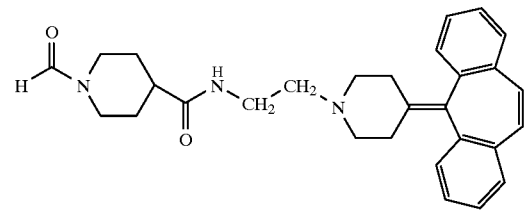

2. The pharmaceutical composition of claim 1 wherein the compound is present in the form of a hydrochloride salt thereof.

3. A method for treating a condition or disease in an individual mediated by serotonin release, selected from the group consisting of ischemic disorders, thrombosis, obstruction, depression, anxiety, diabetic complication, arteriosclerosis migraine, and microcirculation failure, comprising administering a compound, or a pharmaceutically acceptable salt thereof, in a 5HT$_2$ receptor antagonistic effective amount in said individual, wherein said compound has the following formula:

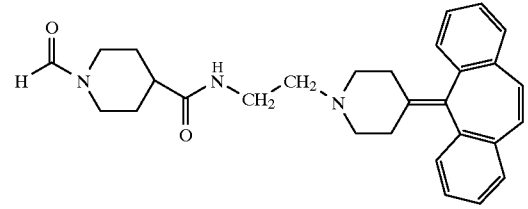

4. The method of claim 3, comprising administering a hydrochloride salt of said compound as the pharmaceutically acceptable salt thereof.

5. The method of claim 3, wherein said effective amount is effective to inhibit platelet aggregation caused by release of serotonin.

6. The method of claim 4, wherein said effective amount is effective to inhibit platelet aggregation caused by release of serotonin.

7. The method of claim 3, wherein said effective amount is effective to inhibit vasoconstriction in vascular smooth muscle caused by release of serotonin.

8. The method of claim 4, wherein said effective amount is effective to inhibit vasoconstriction in vascular smooth muscle caused by release of serotonin.

9. The method of claim 3, wherein the compound is administered in a daily dose of from 0.01 mg to 500 mg by oral administration, or 1 µg to 100 mg by parenteral administration.

10. The method of claim 4, wherein the compound is administered in a daily dose of from 0.01 mg to 500 mg by oral administration, or 1 µg to 100 mg by parenteral administration.

\* \* \* \* \*

UNITED STATES PATENT AND TRADEMARK OFFICE
CERTIFICATE OF CORRECTION

PATENT NO. : 5,932,593

DATED : Aug. 3, 1999

INVENTOR(S): Shingo MAKINO, et al.

It is certified that an error appears in the above-identified patent and that said Letters Patent is hereby corrected as shown below:

Item [73], the Assignee data, is incorrect. It should read as follows:

--[73] Assignee: Ajinomoto Co., Inc., Tokyo, Japan--

Signed and Sealed this

Fourteenth Day of November, 2000

*Attest:*

Q. TODD DICKINSON

*Attesting Officer*         *Director of Patents and Trademarks*